(12) United States Patent
Garcia Molina et al.

(10) Patent No.: US 10,786,174 B2
(45) Date of Patent: Sep. 29, 2020

(54) SYSTEM AND METHOD FOR ADJUSTING THE INTENSITY OF SENSORY STIMULATION DURING SLEEP BASED ON SLEEP SPINDLES

(71) Applicants: KONINKLIJKE PHILIPS N.V., Eindhoven (NL); Wisconsin Alumni Research Association, Madison, WI (US)

(72) Inventors: Gary Nelson Garcia Molina, Madison, WI (US); Michele Bellesi, Madison, WI (US); Stefan Pfundtner, Eindhoven (NL); Brady Alexander Riedner, Middleton, WI (US); Giulio Tononi, Verona, WI (US)

(73) Assignees: KONINKLIJKE PHILIPS N.V., Eindhoven (NL); WISCONSIN ALUMNI RESEARCH FOUNDATION, Madison, WI (US)

( * ) Notice: Subject to any disclaimer, the term of this patent is extended or adjusted under 35 U.S.C. 154(b) by 445 days.

(21) Appl. No.: 15/320,795

(22) PCT Filed: Jul. 6, 2015

(86) PCT No.: PCT/IB2015/055074
§ 371 (c)(1),
(2) Date: Dec. 21, 2016

(87) PCT Pub. No.: WO2016/005870
PCT Pub. Date: Jan. 14, 2016

(65) Prior Publication Data
US 2017/0196474 A1    Jul. 13, 2017

Related U.S. Application Data

(60) Provisional application No. 62/021,333, filed on Jul. 7, 2014.

(51) Int. Cl.
*A61B 5/0484* (2006.01)
*A61B 5/00* (2006.01)
*A61B 5/048* (2006.01)

(52) U.S. Cl.
CPC .......... *A61B 5/04845* (2013.01); *A61B 5/048* (2013.01); *A61B 5/4812* (2013.01); *A61B 5/6803* (2013.01); *A61B 5/6831* (2013.01)

(58) Field of Classification Search
None
See application file for complete search history.

(56) References Cited

U.S. PATENT DOCUMENTS 3,884,218 A    5/1975 Monroe
2006/0293608 A1    12/2006 Rothman et al.
(Continued)

FOREIGN PATENT DOCUMENTS

JP    2009213707 A    9/2009
JP    2011083474 A    4/2011

OTHER PUBLICATIONS

Brain Products, Easycap—SIGGI II: Signal Generator & Impedance Meter, Downloaded From http://www.brainproducts.com/productdetails.php?id=30&tab=2/ on Dec. 21, 2016, 1 Page.
(Continued)

*Primary Examiner* — Etsub D Berhanu

(57) ABSTRACT

The present disclosure pertains to a system configured to adjust an intensity of sensory stimulation delivered to a subject during a sleep session based on sleep spindles in the subject during the sleep session. The system is configured to adjust the intensity of the stimulation based on a sleep spindle frequency and/or a sleep spindle density. The system is configured to determine a recent spindle density and/or a recent spindle frequency for a recent period of time during the sleep session based on detected sleep spindles, and to determine a previous spindle density and/or a previous (Continued)

spindle frequency for a previous period of time during the sleep session based on the detected sleep spindles. The system controls the intensity of sensory stimulation provided to the subject based on a comparison of the previous spindle density to the recent spindle density and/or the previous spindle frequency to the recent spindle frequency.

14 Claims, 8 Drawing Sheets

(56) References Cited

U.S. PATENT DOCUMENTS

| | | |
|---|---|---|
| 2009/0192556 A1 | 7/2009 | Wu et al. |
| 2013/0267866 A1 | 10/2013 | Nakashima et al. |
| 2014/0031712 A1 | 1/2014 | Herskovitz et al. |
| 2014/0269224 A1* | 9/2014 | Huh .................... G04G 13/021 368/73 |
| 2016/0082222 A1 | 3/2016 | Garcia Molina et al. |

OTHER PUBLICATIONS

Tononi et al, "Sleep Function and Synaptic Homeostasis.," Sleep Med. Rev., vol. 10, No. 1, pp. 49-62, Feb. 2006.

Riedner, "Enhancing Sleep Slow Waves With Natural Stimuli," Medicamundi, vol. 45, No. 2, pp. 82-88, 2010.

Dang-Vu, "Spontaneous Brain Rhythms Predict Sleep Stability in the Face of Noise.," Curr. Biol., vol. 20, No. 15, pp. R626-R627, Aug. 2010.

Himanen, "Spindle Frequencies in Sleep EEG Show U-Shape Within First Four NREM Sleep Episodes.," J. Sleep Res., vol. 11, No. 1, pp. 35-42, Mar. 2002.

Andrillon, "Sleep Spindles in Humans: Insights From Intracranial EEG and Unit Recordings.," J. Neurosci., vol. 31, No. 49, pp. 17821-17834, Dec. 2011.

Mccormick, "Sleep and Arousal: Thalamocortical Mechanisms.," Annu. Rev. Neurosci., vol. 20, pp. 185-215, Jan. 1997.

* cited by examiner

SYSTEM AND METHOD FOR ADJUSTING THE INTENSITY OF SENSORY STIMULATION DURING SLEEP BASED ON SLEEP SPINDLES

CROSS-REFERENCE TO PRIOR APPLICATIONS

This application is the U.S. National Phase application under 35 U.S.C. § 371 of International Application Serial No. PCT/IB2015/055074, filed on Jul. 6, 2015, which claims the benefit of U.S. Application Ser. No. 62/021,333, filed on Jul. 7, 2014. These applications are hereby incorporated by reference herein.

BACKGROUND

1. Field

The present disclosure pertains to a system configured to adjust an intensity of sensory stimulation delivered to a subject during a sleep session based on sleep spindles in the subject during the sleep session.

2. Description of the Related Art

Systems for monitoring sleep are known. Sensory stimulation during sleep is known. Sensory stimulation during sleep is often applied continuously and/or at intervals and intensities that do not correspond to sleeping patterns of a subject. The present disclosure overcomes deficiencies in prior art systems.

SUMMARY

Accordingly, one or more aspects of the present disclosure relate to a system configured to adjust an intensity of sensory stimulation delivered to a subject during a sleep session. The system comprises one or more sensory stimulators, one or more sensors, one or more physical computer processors, and/or other components. The one or more sensory stimulators are configured to provide sensory stimulation to the subject. The one or more sensors are configured to generate output signals conveying information related to sleep spindles in the subject during the sleep session. The one or more physical computer processors are configured, by computer readable instructions, to: detect the sleep spindles in the subject based on the output signals; determine a recent spindle density and/or a recent spindle frequency for a recent period of time during the sleep session based on the detected sleep spindles; determine a previous spindle density and/or a previous spindle frequency for a previous period of time during the sleep session based on the detected sleep spindles, wherein a beginning of the previous period of time occurs before a beginning of the recent period of time during the sleep session; and control the one or more sensory stimulators to adjust the intensity of sensory stimulation provided to the subject based on a comparison of the previous spindle density to the recent spindle density and/or the previous spindle frequency to the recent spindle frequency.

Yet another aspect of the present disclosure relates to a method for adjusting an intensity of sensory stimulation delivered to a subject during a sleep session with an adjustment system. The adjustment system comprises one or more sensory stimulators, one or more sensors, one or more physical computer processors, and/or other components. The method comprises providing sensory stimulation to the subject with the one or more sensory stimulators; generating, with the one or more sensors, output signals conveying information related to sleep spindles in the subject during the sleep session; detecting, with the one or more physical computer processors, the sleep spindles in the subject based on the output signals; determining, with the one or more physical computer processors, a recent spindle density and/or a recent spindle frequency for a recent period of time during the sleep session based on the detected sleep spindles; determining, with the one or more physical computer processors, a previous spindle density and/or a previous spindle frequency for a previous period of time during the sleep session based on the detected sleep spindles, wherein a beginning of the previous period of time occurs before a beginning of the recent period of time during the sleep session; and controlling, with the one or more physical computer processors, the one or more sensory stimulators to adjust the intensity of sensory stimulation provided to the subject based on a comparison of the previous spindle density to the recent spindle density and/or the previous spindle frequency to the recent spindle frequency.

Still another aspect of present disclosure relates to a system configured to adjust an intensity of sensory stimulation delivered to a subject during a sleep session. The system comprises means for providing sensory stimulation to the subject; means for generating output signals conveying information related to sleep spindles in the subject during the sleep session; means for detecting the sleep spindles in the subject based on the output signals; means for determining a recent spindle density and/or a recent spindle frequency for a recent period of time during the sleep session based on the detected sleep spindles; means for determining a previous spindle density and/or a previous spindle frequency for a previous period of time during the sleep session based on the detected sleep spindles, wherein a beginning of the previous period of time occurs before a beginning of the recent period of time during the sleep session; and means for controlling the means for providing sensory stimulation to adjust the intensity of sensory stimulation provided to the subject based on a comparison of the previous spindle density to the recent spindle density and/or the previous spindle frequency to the recent spindle frequency.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
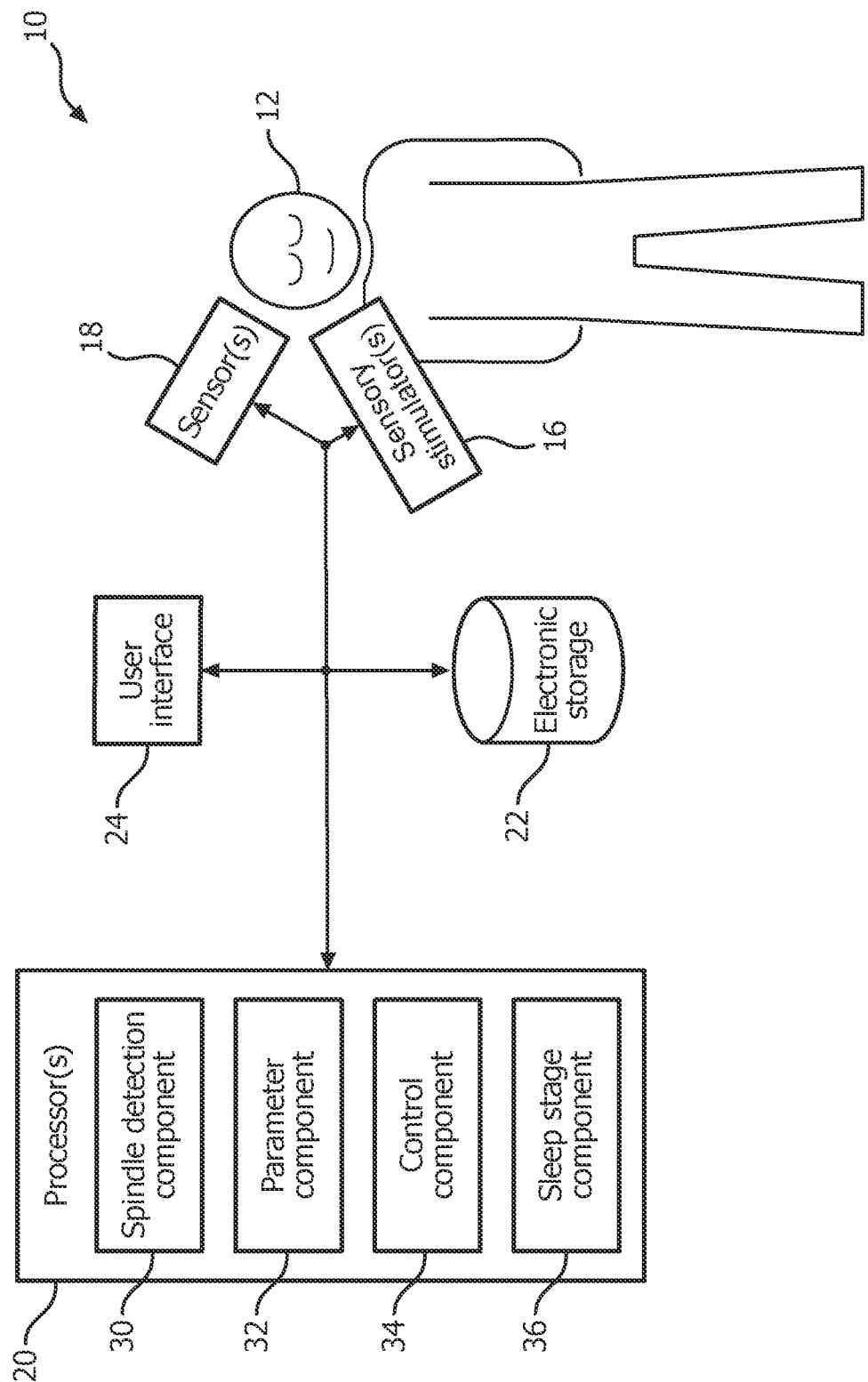
FIG. 1 illustrates a system configured to adjust an intensity of sensory stimulation delivered to a subject during a sleep session based on sleep spindles in the subject during the sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to adjust an intensity of sensory stimulation delivered to a subject 12 during a sleep session based on sleep spindles in the subject during the sleep session. The restorative value of sleep may be increased by enhancing sleep slow waves using sensory (e.g., auditory) stimulation during deep sleep. Sleep slow waves are associated with slow wave activity (SWA) in subject 12 during the sleep session. SWA corresponds to the power of an electroencephalogram (EEG) signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated from an EEG for subject 12 during a given sleep session.

System 10 is configured to adjust, in real-time or near real-time, the intensity (e.g., volume) of sensory stimulation to enhance the slow waves without provoking arousals in subject 12. System 10 is configured to adjust the intensity of the stimulation based on sleep spindles detected in subject 12 during the sleep session. Sleep spindles reflect the activity of the thalamo-cortical network during sleep and are prevalent during deep sleep. A spindle may be characterized as a group of rhythmic waves (e.g., visible via the EEG) with a progressively increasing then gradually decreasing amplitude. Sleep spindles may comprise an electroencephalographic (EEG) hall-mark of non-rapid eye movement (NREM) sleep. Spindles may be classically described as waxing-and-waning 10-16 Hz oscillations lasting about 0.5-2 s. The amplitude of spindles depends on the EEG recording site. Spindles are typically more prominent in central locations (e.g., EEG location Cz). Spindle density is a good indicator of sleep stability (e.g., resistance to sleep disruption). Frequency of spindles decreases as sleep deepens and increases as sleep lightens. System 10 is configured to adjust the intensity (e.g., volume) of the stimulation based on a sleep spindle frequency, a sleep spindle density, and/or other information to enhance SWA without arousing subject 12. For example, if the spindle density increases, a volume, for example, of the stimulation may be increased. If the frequency of spindles decreases, the volume, for example, of the stimulation may be increased.

The sensory stimuli may include different types of sensory stimuli. The different types may include odors, sounds, visual stimulation (e.g., lights flashed on open and/or closed eyes), touches, tastes, and/or other types of sensory stimuli. By way of a non-limiting example, system 10 may be configured to deliver acoustic tones to subject 12. In some embodiments, system 10 may comprise one or more of a sensory stimulator 16, a sensor 18, a processor 20, electronic storage 22, a user interface 24, and/or other components.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices.

Figure 2:
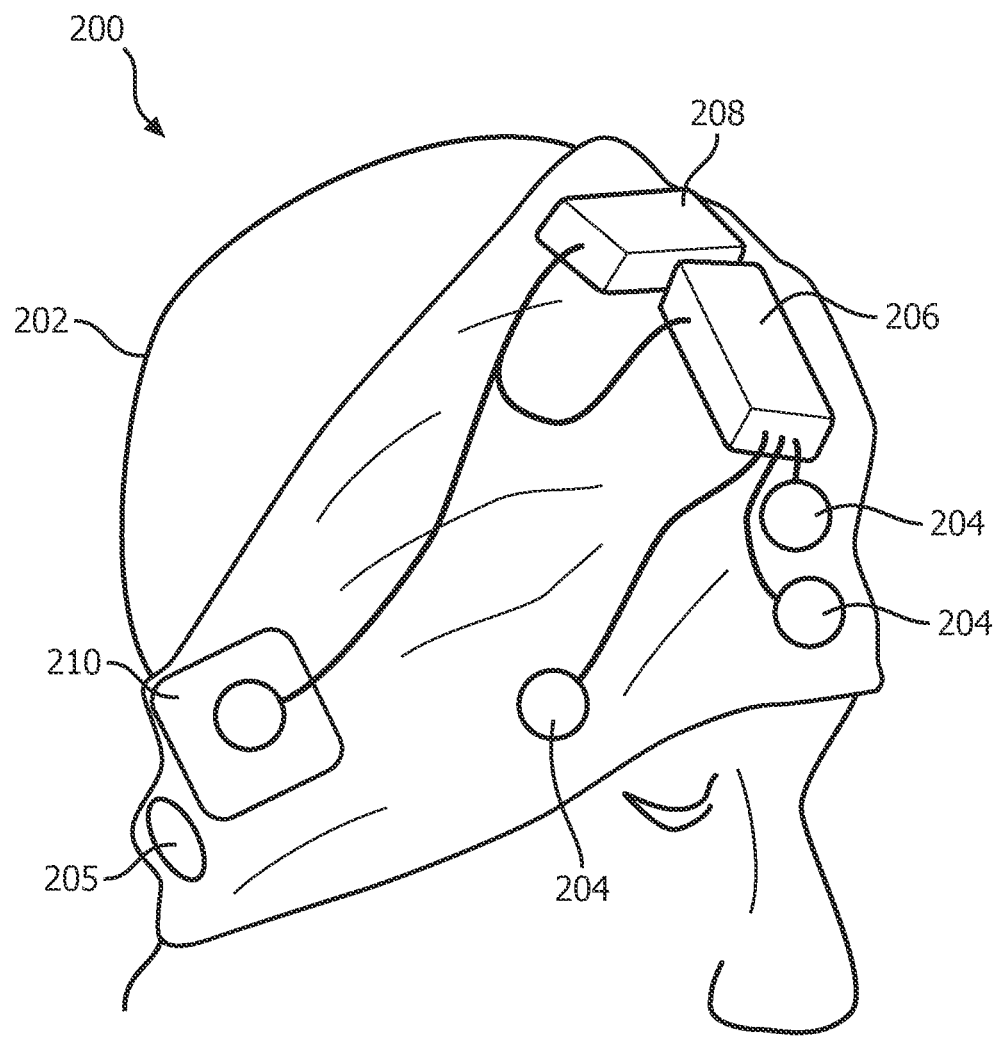
FIG. 2 illustrates a headband worn by a subject.

For example, FIG. 2 illustrates a headband 200 worn by a subject 202. Headband 200 includes sensing electrodes 204, a reference electrode 205, one or more devices associated with an EEG 206, a wireless audio device 208, and one or more audio speakers 210. Audio speakers 210 may be located in and/or near the ears of subject 202. The reference electrode 205 may be located behind the ear of subject 202. In the example shown in FIG. 2, sensing electrodes 204 may be configured to generate output signals conveying information related to the frontal EEG of subject 202, left/right ocular information for subject 202, and/or other information. The output signals may be transmitted to a computing device (e.g., a bedside laptop) wirelessly and/or via wires. Acoustic stimulation may be delivered to subject 202 via wireless audio device 208 and/or speakers 210. An audio signal including information related to auditory stimulation may be generated by the computing device and received by wireless audio device 208. Sensing electrodes 204, reference electrode 205, and devices 206 may be represented, for example, by sensor 18 in FIG. 1. Wireless audio device 208 and speakers 210 may be represented, for example, by sensory stimulator 16 shown in FIG. 1.

Returning to FIG. 1, sensory stimulator 16 is configured to provide sensory stimuli to subject 12. Sensory stimulator 16 is configured to provide sensory stimulation to subject 12 prior to a sleep session, during a sleep session, after a sleep session, and/or at other times. Sensory stimulator 16 is configured to provide sensory stimulation to subject 12 without causing arousals during sleep. For example, sensory stimulator 16 may be configured to provide sensory stimuli to subject 12 during slow wave sleep in a sleep session. Sensory stimulator 16 may be configured to provide sensory stimulation to subject 12 to induce and/or adjust SWA in subject 12. In some embodiments, sensory stimulator 16 may be configured such that inducing and/or adjusting SWA includes inducing, increasing, and/or enhancing sleep slow waves in subject 12.

In some embodiments, sensory stimulator 16 may be configured to induce, increase, and/or enhance sleep slow waves through non-invasive brain stimulation and/or other methods. Sensory stimulator 16 may be configured to induce, increase, and/or enhance sleep slow waves through non-invasive brain stimulation using sensory stimuli. As described above, the sensory stimuli may include odors, sounds, visual stimulation, touches, tastes, and/or other stimuli. For example, acoustic tones may be provided to subject 12 to induce, increase, and/or enhance sleep slow waves. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to sleep spindles in subject 12 during the sleep session, a current sleep stage of subject 12, and/or other information. The current sleep stage of subject 12 may correspond to one or more of non-rapid eye movement (NREM) stage N1, stage N2, or stage N3 sleep, rapid eye movement (REM) sleep, and/or other sleep stages. In some embodiments, NREM stage 3 or stage 2 sleep may be slow wave sleep. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to such parameters indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a spindle detection component 30, a parameter component 32, a control component 34, a sleep stage component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Figure 3:
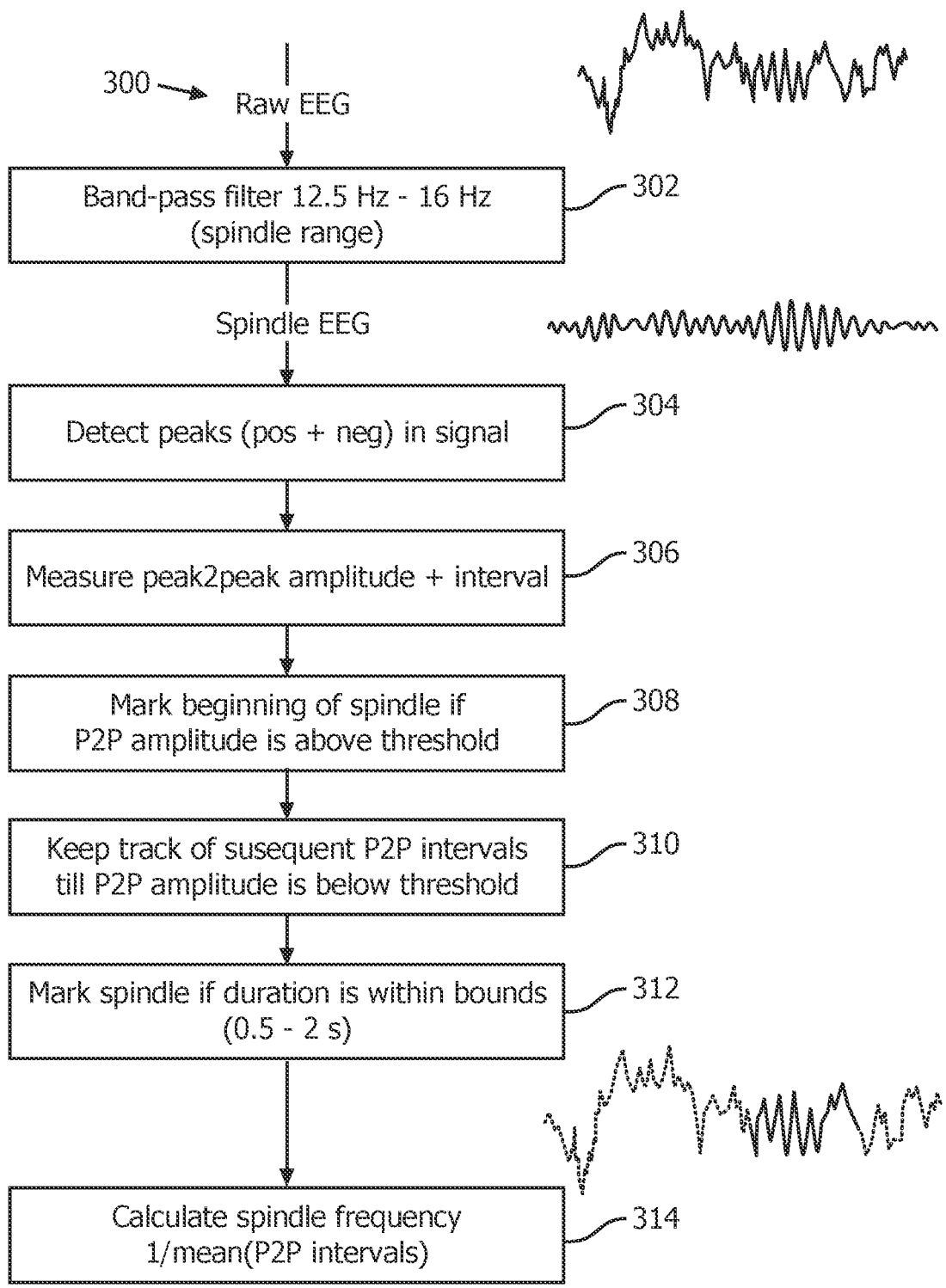
FIG. 3 illustrates sleep spindle detection.

Spindle detection component 30 is configured to detect sleep spindles in subject 12. Spindle detection component 30 is configured to detect the sleep spindles based on the output signals from sensor 18 and/or other information. FIG. 3 illustrates sleep spindle detection. An EEG signal (e.g., output signals from sensor 18) 300 is band-pass filtered in a spindle frequency band (e.g., a range from about 12.5 Hz to about 16 Hz) 302. Positive and negative peaks are detected 304, and the peak-to-peak (peak2peak or P2P) amplitudes and the peak-to-peak-interval durations are determined 306. In some embodiments, typical peak-to-peak amplitudes may be about 10 to about 30 microvolts, for example. In some embodiments, the duration of the spindle event may be about 500 to about 2000 milliseconds, for example. In some embodiments, if a determined amplitude is above a preset threshold ($\tau$) such as about 17 microvolts, for example, the previous positive peak is marked as the beginning of a "candidate-spindle" 308. Subsequent peak-to-peak intervals are stored in a buffer (e.g., electronic storage 22) until the peak-to-peak amplitude decreases to a level that is back below the threshold $\tau$ 310. If the duration of the candidate-spindle falls within a typical spindle-duration range (e.g., about 500 to about 2000 milliseconds), then the candidate-spindle is tagged as a "detected spindle" 312. The average spindle frequency is then determined 314 based on the inverse of the average peak-to-peak-interval duration (see the description of the parameter component below).

Returning to FIG. 1, parameter component 32 is configured to determine one or more parameters related to sleep spindles in subject 12, one or more parameters related to a current sleep stage of subject 12, parameters related to the sensory stimulation provided to subject 12, and/or other parameters. Parameter component 32 is configured to determine parameters based on the output signals from sensor 18, the spindles detected by spindle detection component 30, and/or other information. The parameters may include a quantity of spindles, a spindle density, a spindle frequency, a sleep stage, a sensory stimulation intensity level, a sensory stimulation timing, a number of microarousal events (e.g., a microarousal is a high frequency event occurring in the EEG which has comparatively high amplitudes such as about 50-100 microvolts) during a recent period of time (e.g., the last minute), and/or other parameters.

Parameter component 32 is configured determine a recent spindle density and/or a recent spindle frequency for a recent period of time during the sleep session based on the detected sleep spindles and/or other information. For example, parameter component 32 may determine a spindle density and/or a spindle frequency for the most recent minute of the sleep session. In some embodiments, the recent spindle density and/or frequency may be an average density and/or frequency determined based on multiple density and/or frequency determinations during the most recent minute. In some embodiments, the recent spindle density and/or frequency may indicate a relative change in spindle density and/or frequency from the start of the most recent minute to the end of the most recent minute. In some embodiments, the recent spindle density and/or frequency may be and/or be based on a single density and/or frequency determination.

Parameter component 32 is configured to determine a previous spindle density and/or a previous spindle frequency for a previous period of time during the sleep session based on the detected sleep spindles and/or other information. For example, parameter component 32 may determine a spindle density and/or a spindle frequency for the five minutes of the sleep session leading up to the most recent minute. In some embodiments, the previous spindle density and/or frequency may be an average density and/or frequency determined based on multiple density and/or frequency determinations during the previous period of time. In some embodiments, the previous spindle density and/or frequency may indicate a relative change in spindle density and/or frequency from the start of the previous period of time (e.g., the beginning of the five minute period) to the end of the previous period of time (e.g., the end of the five minute period). In some embodiments, the previous spindle density and/or frequency may be and/or be based on a single density and/or frequency determination.

The spatial arrangement and the periods of time (the durations) for the recent period of time (e.g., one minute) and the previous period of time (e.g., five minutes) described above is not intended to be limiting. The recent period of time and/or the previous period of time may have any length that allows system 10 to function as described herein. In some embodiments, a beginning of the previous period of time occurs before a beginning of the recent period of time during the sleep session. In some embodiments, the previous period of time ends before the recent period of time begins. In some embodiments, the previous period of time ends substantially when the recent period of time begins. In some embodiments, the previous period of time ends after the recent period of time begins (e.g., the previous period of time and the recent period of time overlap). In some embodiments, the spindle densities and/or frequencies determined by parameter component 32 are stored in electronic storage 22.

Control component 34 is configured to control sensory stimulator 16 to adjust the intensity of sensory stimulation provided to subject 12 based on a comparison of the previous spindle density to the recent spindle density and/or the previous spindle frequency to the recent spindle frequency. In some embodiments, control component 34 is configured to cause sensory stimulator 16 to increase the intensity of sensory stimulation responsive to an increase in the recent spindle density relative to the previous spindle density and/or a decrease in the recent spindle frequency relative to the previous spindle frequency. For example, control component 34 is configured to cause sensory stimulator 16 to increase a volume of audible tones responsive to an increase in the recent spindle density relative to the previous spindle density and/or a decrease in the recent spindle frequency relative to the previous spindle frequency. In some embodiments, control component 34 is configured to cause sensory stimulator 16 to decrease the intensity of sensory stimulation responsive to a decrease in the recent spindle density relative to the previous spindle density and/or an increase in the recent spindle frequency relative to the previous spindle frequency. For example, control component 34 is configured to cause sensory stimulator 16 to decrease a volume of the audible tones responsive to a decrease in the recent spindle density relative to the previous spindle density and/or an increase in the recent spindle frequency relative to the previous spindle frequency.

By way of a non-limiting example, if control component 34 detects a change of about +0.1 spindles-per-minute in the recent spindle density with respect to the previous spindle density (e.g., the average of the density values stored in electronic storage for the previous five minutes), control component 34 may control sensory stimulator 16 such that the volume (e.g., for auditory stimulation) of the stimulation is increased by about 6 dBs. If a change of about −0.1 spindles-per-minute is detected, then the volume of the stimulation may be increased by about 6 dBs. If a change of about +0.05 Hz is detected in the recent spindle frequency with respect to the previous spindle frequency, then the volume of the stimulation may be decreased by about 6 dBs. If a change of about −0.05 Hz is detected, then the volume of the stimulation may be increased by about 6 dBs. These examples are not intended to be limiting. The changes of 0.1 in spindle density and/or 0.05 Hz in spindle frequency may be customized for an individual user using based on information from previous sleep sessions of the individual user and/or other information.

Figure 4A:
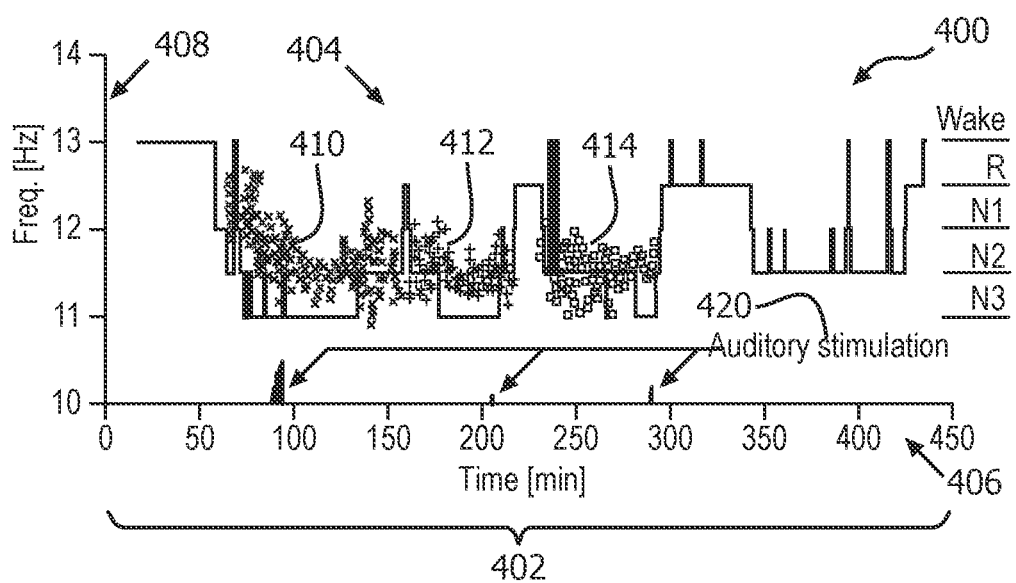
FIG. 4 illustrates a hypnogram for a given subject who received auditory stimulation during a sleep session and sleep spindles that were detected during the sleep session.

FIG. 4 illustrates a hypnogram 400 for a given subject who received auditory stimulation 420 during a sleep session 402 and sleep spindles 404 that were detected during sleep session 402. In FIG. 4A, the detected spindles 404 and the hypnogram 400 are shown for a representative night of sleep by the subject. The horizontal axis 406 indicates the time in minutes from the beginning of the sleep session and the vertical axis 408 indicates the frequency of the detected spindles in Hz. Spindles 410 occur during a first sleep cycle, spindles 412 occur during a second sleep cycle, and spindles 414 occur during a third sleep cycle. A sleep cycle corresponds to an orderly progression through successive sleep stages (described below), from light sleep to deep sleep and then followed by rapid eye movement (REM) sleep. Sleep cycles are detected in real-time based on an EEG, and/or by other methods. Timing and intensity of auditory stimulation 420 delivered to the subject is roughly indicated by the vertical lines rising from horizontal axis 406 (a longer line represents a louder tone). The frequency of the spindles follows a "u-shape" trend within a sleep cycle. A slight trend towards decreasing spindle frequencies is observed across sleep cycles. Within a cycle it is possible to establish a polynomial regression to demonstrate a relationship between the spindle frequency and the time. For the particular example in FIG. 4A, a second-order polynomial provided an appropriate fit-accuracy while preventing overfitting.

Figure 4B:
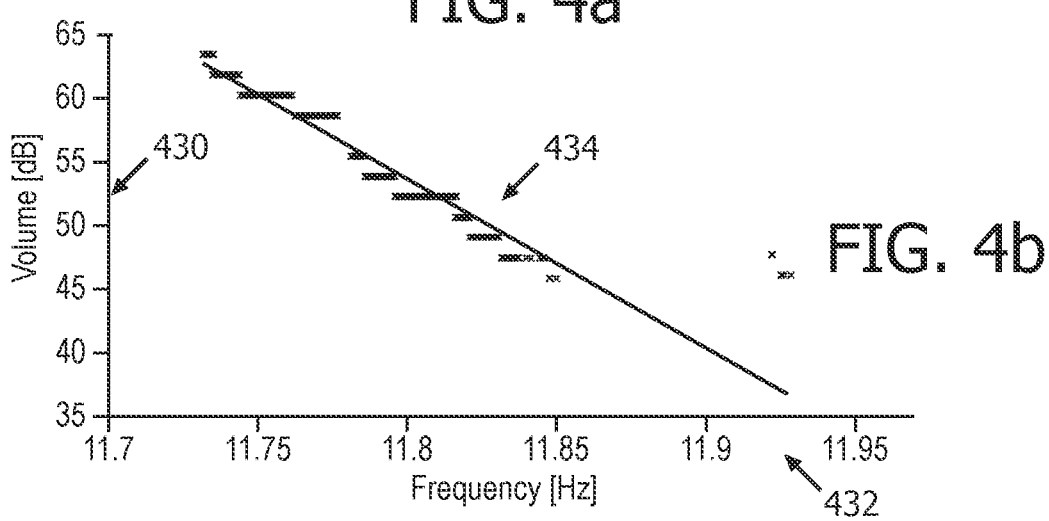
Figure 4C:
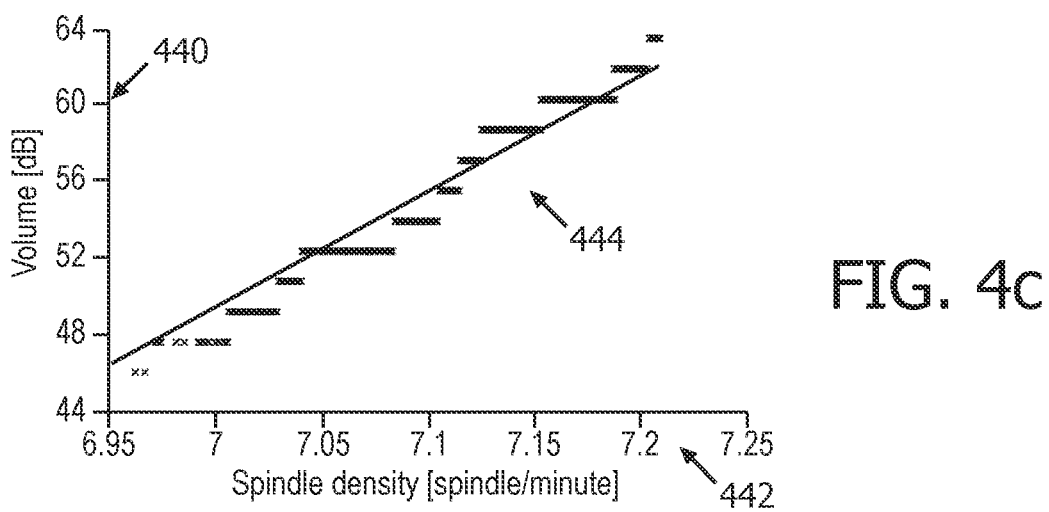

In FIG. 4B, the volume of the tones in decibels (dB) 430 is plotted versus the extrapolated (using the polynomial regression) spindle frequency 432 at the time of the tone. A linear trend 434 indicates that when the volume of the stimulation is higher, the spindle frequency is lower. For this particular example the volume (in decibels) negatively correlates with the frequency through the regression equation: $V \approx 1595.3 - 130.7 \times f$. Thus, a decrease in the spindle frequency of about 0.05 Hz, for example, translates in an increase of the stimulation volume of about 6.5 decibels. In FIG. 4C, the volume of the tones in decibels (dB) 440 is plotted versus the extrapolated (using a second order polynomial regression) spindle density (in spindles per minute) 442 at the time of the tone. A linear trend 444 indicates that when the volume of the stimulation was higher, the spindle density was higher. For this particular example, the volume (in decibels) positively correlates with the spindle density ($\delta$) through the regression equation: $V \approx -372.7 + 60.3 \times \delta$. Thus, an increase in the spindle density of about 0.1 spindles/minute, for example, translates to an increase of the stimulation volume of about 6 decibels.

Returning to FIG. 1, in some embodiments, control component 34 is configured such that the intensity (e.g., volume) of the stimulation is not always adjusted responsive to spindle density and/or spindle frequency changes. In some embodiments, (e.g., where the stimulation is already at a predetermined maximum intensity in deep sleep and the spindle density decreases), system 10 may be configured such that a decrease in spindle density does not affect the intensity of the stimulation.

In some embodiments, control component 34 is configured to control sensory stimulator 16 to provide the sensory stimulation during the sleep session such that the sensory stimulation does not unintentionally wake subject 12. Controlling sensory stimulator 16 to provide sensory stimulation so subject 12 is not unintentionally aroused from sleep may be accomplished by controlling the timing, frequency, intensity, and/or other parameters of the stimulation. For example, control component 34 may cause sensory stimulator 16 to deliver acoustic stimulation to subject 12 to increase sleep slow waves just after subject 12 has fallen asleep, and not while subject 12 is falling asleep.

In some embodiments, control component 34 is configured to detect a possible arousal event in subject 12 based on the output signals. In some embodiments, control component 34 is configured to detect possible arousal events, and/or the likelihood of producing arousals based on the instantaneous EEG power in the beta band (described below), and/or by other methods. An arousal event may include waking from sleep and/or other arousal events associated with wakefulness of subject 12. Responsive to detecting the possible arousal event, control component 34 may cause sensory stimulator 16 to cease providing sensory stimulation and then determine whether the possible arousal event was a false arousal event. Responsive to determining that the possible arousal event was a false arousal event, control component 34 may cause sensory stimulator 16 to resume providing sensory stimulation with an intensity determined based on the recent spindle density relative to the previous spindle density and/or the recent spindle frequency relative to the previous spindle frequency.

Figure 5:
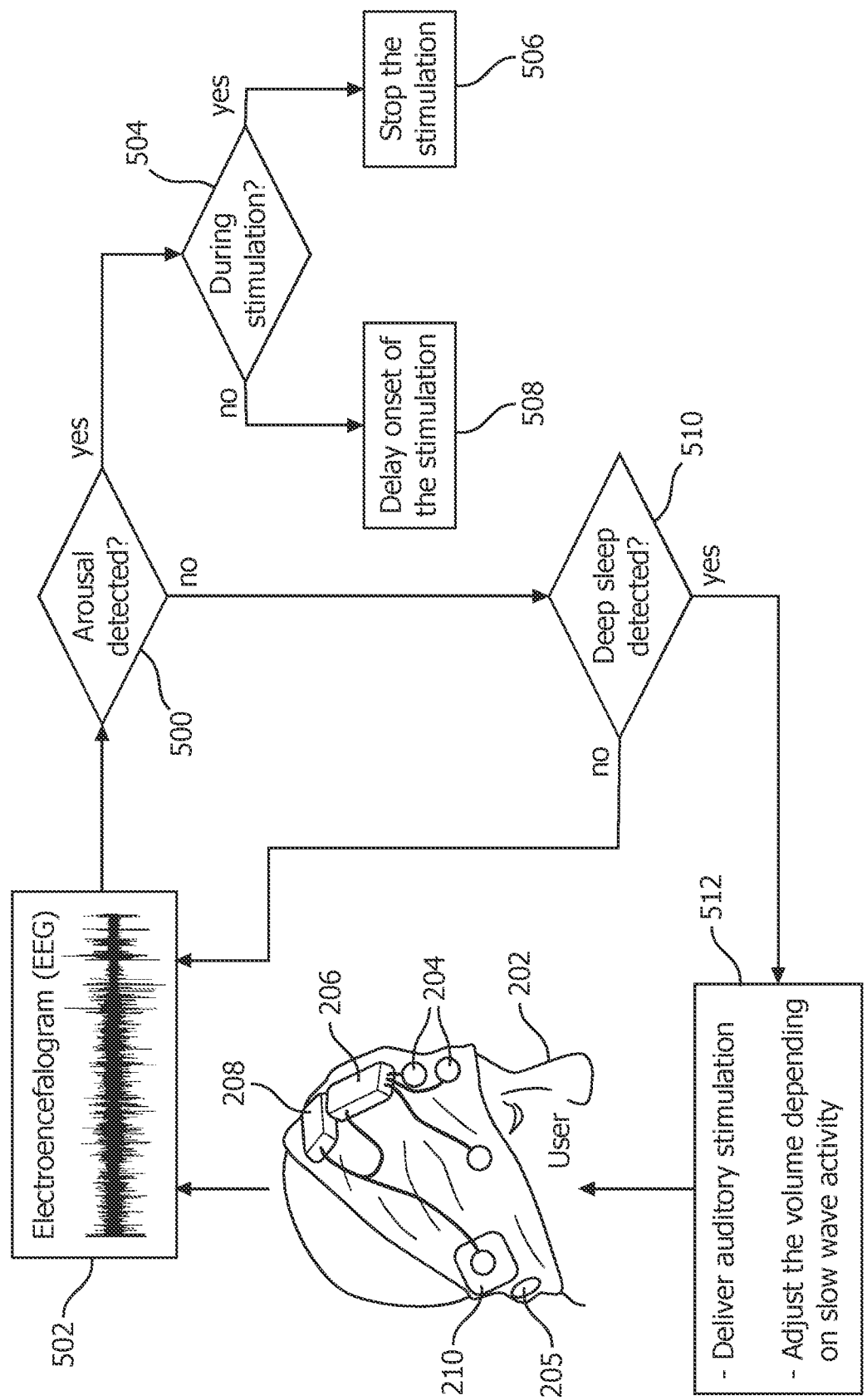
FIG. 5 illustrates delaying and/or stopping sensory stimulation responsive to detecting a possible arousal event.

For example, FIG. 5 illustrates delaying and/or stopping sensory stimulation responsive to detecting a possible arousal event. Control component 34 (FIG. 1) is configured to control sensory stimulator 210 such that a volume of auditory stimulation (for example) is first provided at a level that is approximately equal to a hearing threshold (e.g., subjectively determined via a calibration during wakefulness) of a subject and then progressively adjusted (e.g., increased) as described above (based on the detected sleep spindles). (In some embodiments, an upper limit for the intensity of the sensory stimulation (e.g., volume) may also be subjectively determined during a previous calibration.) Possible arousal events 500 are detected based on EEG signals 502 (e.g., output signals from sensor 18). If a possible arousal is detected by system 10 during stimulation 504, control component 34 (FIG. 1) controls a sensory stimulator 210 such that the stimulation stops 506. If an arousal is detected outside the stimulation period, the onset of the stimulation is delayed 508. If no arousal is detected, then the system attempts to detect deep sleep 510. If deep sleep is detected, the auditory stimulation is delivered 512. As described above, responsive to determining that the possible arousal event was a false arousal event, control component 34 may cause sensory stimulator 210 to resume providing sensory stimulation with an intensity determined based on the recent spindle density relative to the previous spindle density and/or the recent spindle frequency relative to the previous spindle frequency. System 10 does not automatically revert back to the lowest intensity level in such situations.

Figure 6:
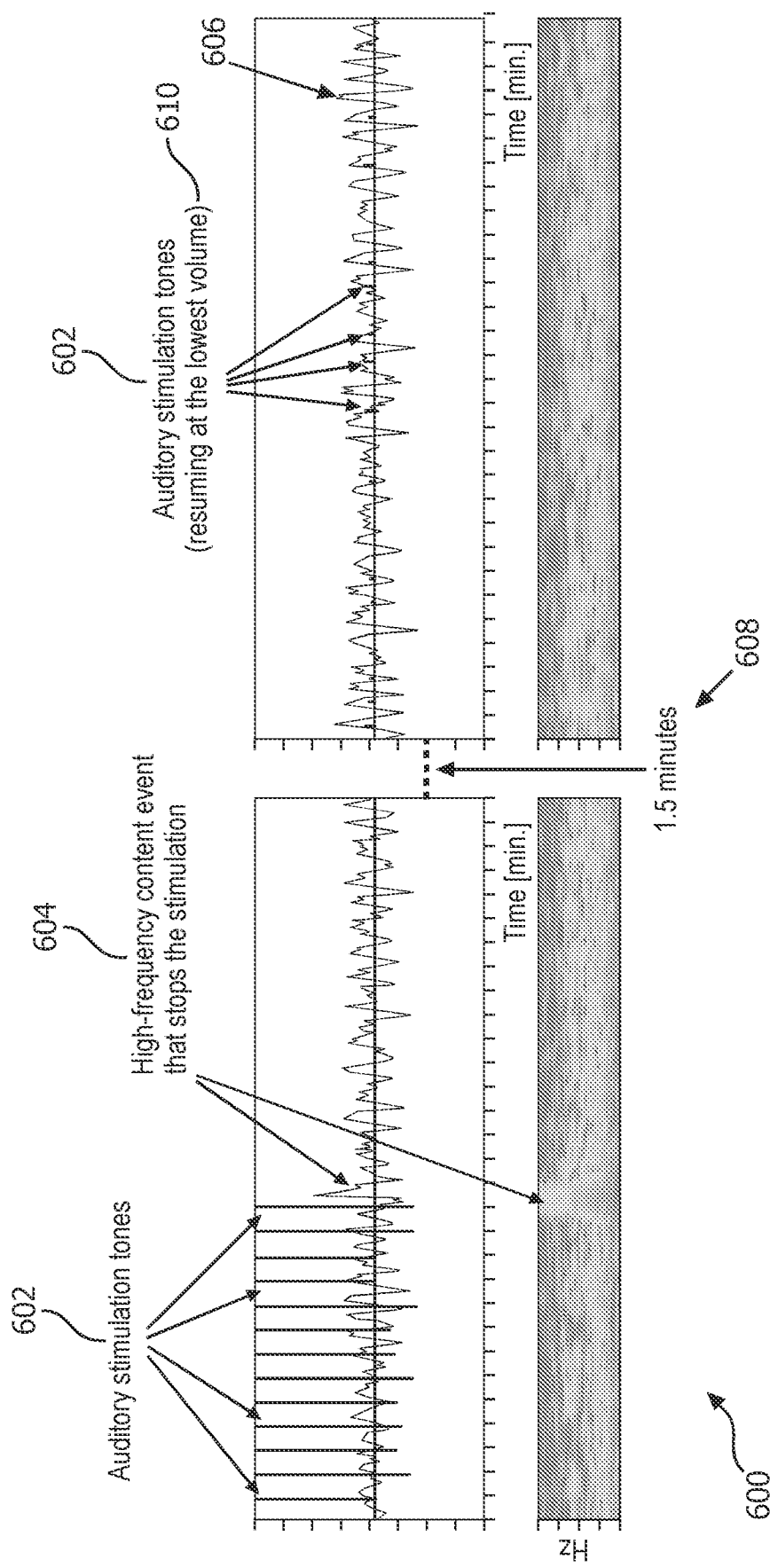
FIG. 6 illustrates a sleep session where the provided stimulation is interrupted due to the detection of a possible event with high-frequency content which is determined by the system to be an arousal.

In contrast, responsive to detecting a possible arousal event (whether false or actual), prior art systems automatically revert back to their lowest sensory stimulation intensity level when restarting delivery of sensory stimulation to a subject. For example, FIG. 6 illustrates a sleep session where the stimulation 602 provided by a prior art system is interrupted due to the detection of a possible event 604 with high-frequency content which is determined by the system to be an arousal. Even if slow-wave sleep continues and large slow-waves are visible in the EEG 606, the stimulation 602 resumes only after more than 1.5 minutes 608 have passed. In addition, the stimulation starts at the lowest volume 610 which constitutes a loss of opportunity to stimulate. System 10 overcomes this inefficiency by resuming the provision of sensory stimulation with an intensity determined based on the recent spindle density relative to the previous spindle density and/or the recent spindle frequency relative to the previous spindle frequency. System 10 does not automatically revert back to a lowest intensity level to restart sensory stimulation. System 10 is configured such that the intensity of the acoustic stimulation is adjusted according to the level of thalamo-cortical polarization (e.g., as indicated by detected sleep spindles) in order to avoid undesired arousals and sleep fragmentation.

Returning to FIG. 1, sleep stage component 36 is configured to determine the sleep stage of subject 12 one or more times during the sleep session. Sleep stage component 36 is configured to determine the sleep stage based on the output signals, the detected spindles, an EEG, and/or other information. Sleep stages of subject 12 may include one or more of NREM stage N1, stage N2, or stage N3 sleep, REM sleep, and/or other sleep stages. In some embodiments, N1 and/or N2 corresponds to a light sleep state and N3 corresponds to a deep sleep state. In some embodiments, NREM stage N3 or stage N2 sleep may be slow wave (e.g., deep) sleep. In some embodiments, slow waves may not be present throughout the whole N3 period, for example, but it may be significantly more likely that such slow waves are present during N3. Slow waves may also be present (although to a lesser extent) during N2, for example. In some embodiments, sleep stage component 36 determines sleep stages based amounts of power in one or more bands of the EEG (e.g., beta, spindle, alpha, theta, delta), and/or related to other characteristics of the brain activity of subject 12. Typical band-limit values are about 8-12 Hz (alpha), about 15-30 Hz (beta), about 11-16 Hz (sigma/spindle), about 30-60 Hz (gamma), about 0.5-4 Hz (delta), and/or about 4-8 Hz (theta). In some embodiments, sleep stage component 36 determines deep sleep based on a logarithm of the ratio between the beta and delta power (log(beta/delta)). For example, if this ratio is less than −3, then subject 12 is sleeping deeply.

In some embodiments, control component 34 is configured to control sensory stimulator 16 to adjust the intensity of the stimulation based on the sleep stage determinations by sleep stage component 36. For example, the volume of auditory stimulation may be increased when log(beta/delta) has a decreasing trend over time. Control component 34 may be configured to control sensory stimulator 16 to adjust the intensity of the stimulation based on the sleep stage determinations in addition to and/or instead of controlling sensory stimulator 16 based on the changes in spindle density, the changes in spindle frequency, and/or other information.

Figure 7:
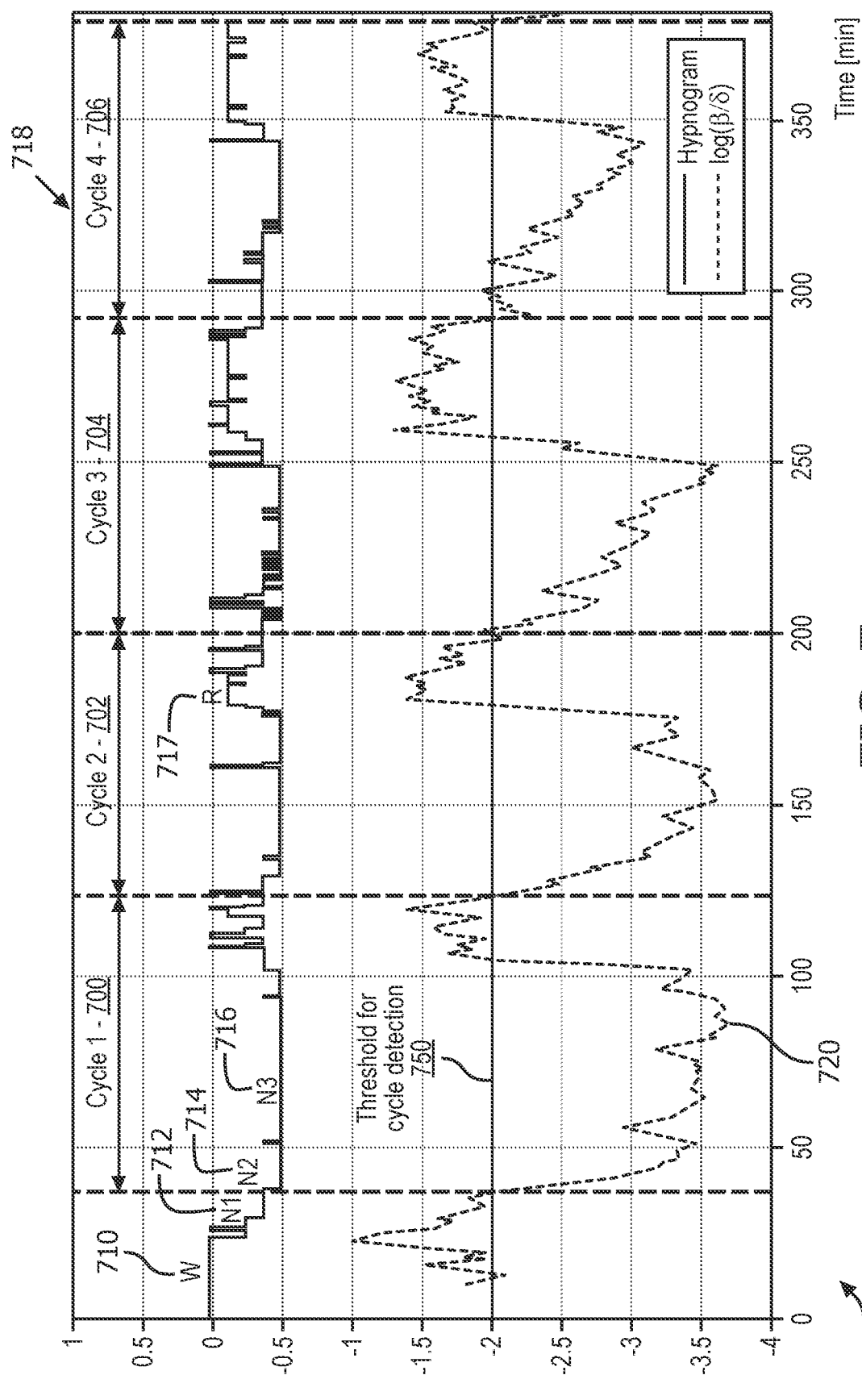
FIG. 7 illustrates four sleep cycles within a sleep session.

For example, FIG. 7 illustrates four sleep cycles 700, 702, 704, 706 within a sleep session 708. As described above, a sleep cycle corresponds to an orderly progression through successive sleep stages, from light sleep to deep sleep and then followed by rapid eye movement (REM) sleep. The orderly progression through successive sleep stages 710 (wakefulness), 712 (N1), 714 (N2), 716 (N3), 717 (REM) is illustrated in hypnogram 718. The logarithm of the ratio between the beta and delta power 720 indicates sleep depth. If this ratio breaches a threshold of −2, for example, a sleep cycle may be starting and/or ending 750. If this ratio is lower than −3, for example, then the sleep is at its deepest. In some embodiments, the volume of the stimulation is increased when log(beta/delta) has a decreasing trend (e.g., which can be estimated using a 30-second long window).

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 8:
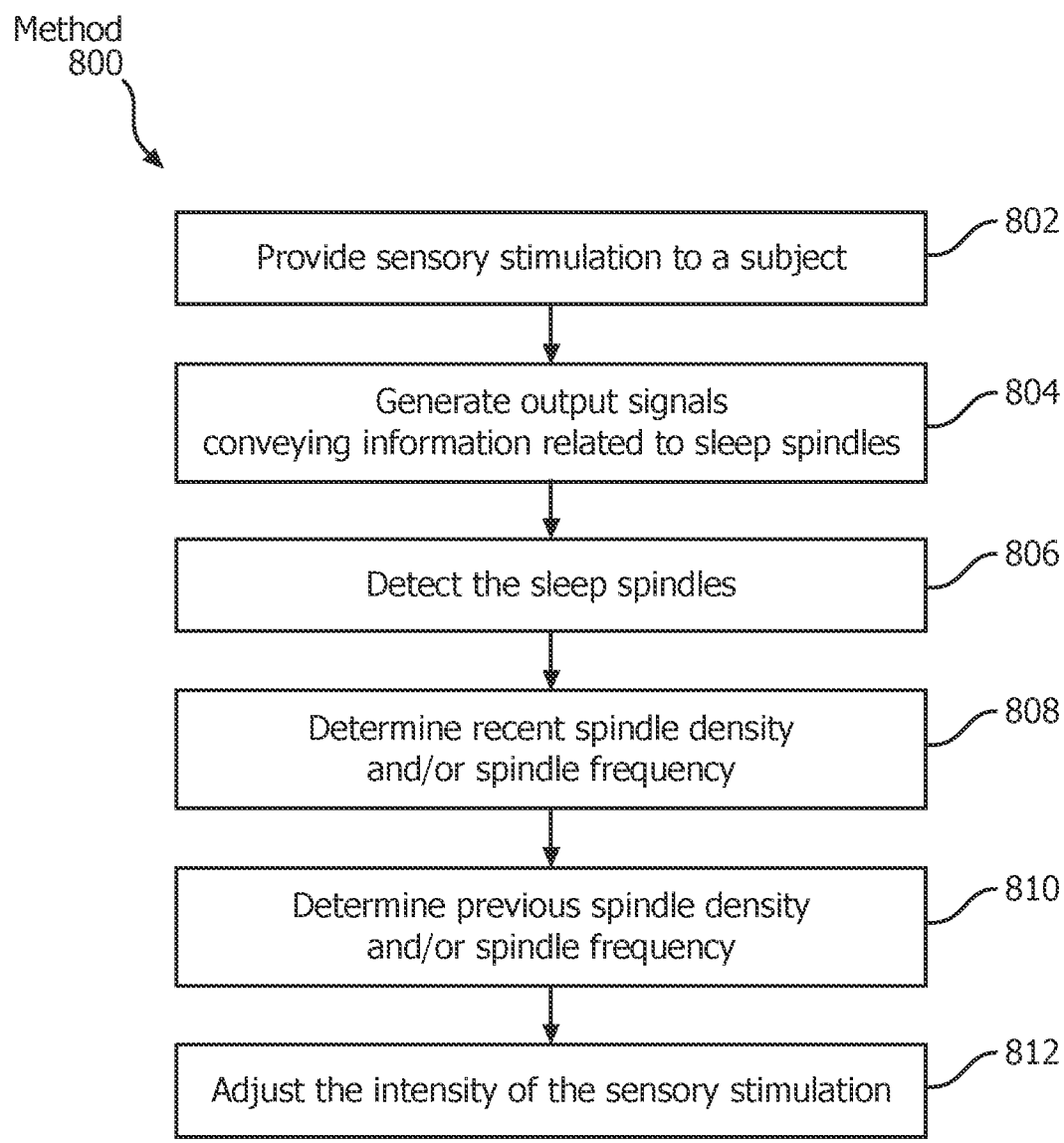
FIG. 8 illustrates a method for adjusting an intensity of sensory stimulation delivered to a subject during a sleep session with an adjustment system.

FIG. 8 illustrates a method 800 for adjusting an intensity of sensory stimulation delivered to a subject during a sleep session with an adjustment system. The system comprises one or more sensory stimulators, one or more sensors, one or more processors, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, sensory stimulation is provided to a subject. In some embodiments, the sensory stimulation is and/or includes audible tones. The sensory stimulation may be provided prior to a sleep session, during a sleep session, after a sleep session, and/or at other times. The sensory stimulation may be provided without causing arousals during sleep. For example, sensory stimuli may be provided to subject during slow wave sleep in a sleep session. In some embodiments, operation 802 is performed by one or more sensory stimulators the same as or similar to sensory stimulator 16 (shown in FIG. 1 and described herein).

At an operation 804, output signals conveying information related to sleep spindles in the subject during a sleep session, information related to a recent sleep stage of the subject, and/or other information are generated. In some embodiments, operation 804 is performed by one or more sensors the same as or similar to sensors 18 (shown in FIG. 1 and described herein).

At an operation 806, sleep spindles in the subject are detected. Sleep spindles are detected based on the output signals. In some embodiments, operation 806 is performed by a physical computer processor the same as or similar to processor 20 (shown in FIG. 1 and described herein).

At an operation 808, a recent spindle density and/or spindle frequency is determined. The recent spindle density and/or spindle frequency is determined for a recent period of time during the sleep session based on the detected sleep spindles. In some embodiments, operation 808 is performed by a physical computer processor the same as or similar to processor 20 (shown in FIG. 1 and described herein).

At an operation 810, a previous spindle density and/or spindle frequency is determined. The previous spindle density and/or spindle frequency is determined for a previous period of time during the sleep session based on the detected sleep spindles. A beginning of the previous period of time occurs before a beginning of the recent period of time during the sleep session. In some embodiments, operation 810 is performed by a physical computer processor the same as or similar to processor 20 (shown in FIG. 1 and described herein).

At an operation 812, an intensity of the sensory stimulation provided to the subject is adjusted. The one or more sensory stimulators are controlled to adjust the intensity of sensory stimulation provided to the subject based on a comparison of the previous spindle density to the recent spindle density and/or the previous spindle frequency to the recent spindle frequency. In some embodiments, an intensity of the sensory stimulation (e.g., a volume of audible tones) is increased responsive to an increase in the recent spindle density relative to the previous spindle density or a decrease in the recent spindle frequency relative to the previous spindle frequency. In some embodiments, an intensity of the sensory stimulation (e.g., a volume of audible tones) is decreased responsive to a decrease in the recent spindle density relative to the previous spindle density or an increase in the recent spindle frequency relative to the previous spindle frequency. In some embodiments, operation 812 is performed by a physical computer processor the same as or similar to processor 20 (shown in FIG. 1 and described herein).

In some embodiments, operation 812 includes determining a sleep stage of the subject based on the output signals and adjusting the intensity of sensory stimulation based on the determined sleep stage. In some embodiments, operation 812 includes detecting a possible arousal event based on the output signals; responsive to detecting the possible arousal event, causing the one or more sensory stimulators to cease providing sensory stimulation; determining whether the possible arousal event was a false arousal event; and responsive to determining that the possible arousal event was a false arousal event, causing the one or more sensory stimulators to resume providing sensory stimulation with an intensity determined based on the recent spindle density relative to the previous spindle density and/or the recent spindle frequency relative to the previous spindle frequency.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to adjust an intensity of sensory stimulation delivered to a subject during a sleep session, the system comprising:
one or more sensory stimulators configured to provide sensory stimulation to the subject;
one or more sensors configured to generate output signals conveying information related to sleep spindles in the subject during the sleep session; and
one or more physical computer processors configured by computer readable instructions to:
detect the sleep spindles in the subject based on the output signals;
determine a recent spindle density and/or a recent spindle frequency for a recent period of time during the sleep session based on the detected sleep spindles;
determine a previous spindle density and/or a previous spindle frequency for a previous period of time during the sleep session based on the detected sleep spindles, wherein a beginning of the previous period of time occurs before a beginning of the recent period of time during the sleep session;
control the one or more sensory stimulators to adjust the intensity of sensory stimulation provided to the subject based on a comparison of the previous spindle density to the recent spindle density and/or the previous spindle frequency to the recent spindle frequency, wherein controlling the one or more sensory stimulators includes, responsive to the recent spindle density and the previous spindle density being determined, increasing the intensity of the sensory stimulation responsive to an increase in the recent spindle density relative to the previous spindle density;
detect a possible arousal event based on the output signals;
responsive to detecting the possible arousal event, cause the one or more sensory stimulators to cease providing sensory stimulation;
determine whether the possible arousal event was a false arousal event; and
responsive to determining that the possible arousal event was a false arousal event, cause the one or more sensory stimulators to resume providing sensory stimulation with an intensity determined based on the recent spindle density relative to the previous spindle density and/or the recent spindle frequency relative to the previous spindle frequency.

2. The system of claim 1, wherein the one or more sensory stimulators are configured such that the sensory stimulation comprises audible tones, and wherein the one or more physical computer processors are configured to cause the one or more sensory stimulators to increase a volume of the audible tones responsive to the increase in the recent spindle density relative to the previous spindle density or, responsive to the recent spindle frequency and the previous spindle frequency being determined, a decrease in the recent spindle frequency relative to the previous spindle frequency.

3. The system of claim 1, wherein the one or more sensory stimulators are configured such that the sensory stimulation comprises audible tones, and wherein the one or more physical computer processors are configured to cause the one or more sensory stimulators to decrease a volume of the audible tones responsive to a decrease in the recent spindle density relative to the previous spindle density or, responsive to the recent spindle frequency and the previous spindle frequency being determined, an increase in the recent spindle frequency relative to the previous spindle frequency.

4. The system of claim 1, wherein the previous period of time ends at the same time as, or immediately before, the recent period of time begins during the sleep session.

5. The system of claim 1, wherein the previous period of time ends after the recent period of time begins such that the previous period of time and the recent period of time overlap during the sleep session.

6. The system of claim 1, wherein the one or more sensors are configured such that the output signals convey information related to a sleep stage of the subject during the sleep session; and
wherein the one or more physical computer processors are further configured to determine the sleep stage of the subject based on the output signals and control the one or more sensory stimulators to adjust the intensity of the stimulation based on the determined sleep stage.

7. A method for adjusting an intensity of sensory stimulation delivered to a subject during a sleep session with an adjustment system, the adjustment system comprising one or more sensory stimulators, one or more sensors, and one or more physical computer processors, the method comprising:
providing sensory stimulation to the subject with the one or more sensory stimulators;
generating, with the one or more sensors, output signals conveying information related to sleep spindles in the subject during the sleep session;
detecting, with the one or more physical computer processors, the sleep spindles in the subject based on the output signals;
determining, with the one or more physical computer processors, a recent spindle density and/or a recent spindle frequency for a recent period of time during the sleep session based on the detected sleep spindles;
determining, with the one or more physical computer processors, a previous spindle density and/or a previous spindle frequency for a previous period of time during the sleep session based on the detected sleep spindles, wherein a beginning of the previous period of time occurs before a beginning of the recent period of time during the sleep session; and
controlling, with the one or more physical computer processors, the one or more sensory stimulators to adjust the intensity of sensory stimulation provided to the subject based on a comparison of the previous spindle density to the recent spindle density and/or the previous spindle frequency to the recent spindle frequency, wherein controlling the one or more sensory stimulators includes, responsive to the recent spindle density and the previous spindle density being determined, increasing the intensity of the sensory stimulation responsive to an increase in the recent spindle density relative to the previous spindle density;
detecting a possible arousal event based on the output signals;
responsive to detecting the possible arousal event, causing the one or more sensory stimulators to cease providing sensory stimulation;
determining whether the possible arousal event was a false arousal event; and
responsive to determining that the possible arousal event was a false arousal event, causing the one or more sensory stimulators to resume providing sensory stimulation with an intensity determined based on the recent spindle density relative to the previous spindle density and/or the recent spindle frequency relative to the previous spindle frequency.

8. The method of claim 7, wherein the sensory stimulation comprises audible tones, and wherein a volume of the audible tones is increased responsive to the increase in the recent spindle density relative to the previous spindle density or, responsive to the recent spindle frequency and the previous spindle frequency being determined, a decrease in the recent spindle frequency relative to the previous spindle frequency.

9. The method of claim 7, wherein the sensory stimulation comprises audible tones, and wherein a volume of the audible tones is decreased responsive to a decrease in the recent spindle density relative to the previous spindle density or, responsive to the recent spindle frequency and the previous spindle frequency being determined, an increase in the recent spindle frequency relative to the previous spindle frequency.

10. The method of claim 7, wherein the one or more sensors are configured such that the output signals convey information related to a sleep stage of the subject during the sleep session, the method further comprising;
determining the sleep stage of the subject based on the output signals; and
controlling the one or more sensory stimulators to adjust the intensity of the stimulation based on the determined sleep stage.

11. A system configured to adjust an intensity of sensory stimulation delivered to a subject during a sleep session, the system comprising:
means for providing sensory stimulation to the subject;
means for generating output signals conveying information related to sleep spindles in the subject during the sleep session;
means for detecting the sleep spindles in the subject based on the output signals;
means for determining a recent spindle density and/or a recent spindle frequency for a recent period of time during the sleep session based on the detected sleep spindles;
means for determining a previous spindle density and/or a previous spindle frequency for a previous period of time during the sleep session based on the detected sleep spindles, wherein a beginning of the previous period of time occurs before a beginning of the recent period of time during the sleep session;
means for controlling the means for providing sensory stimulation to adjust the intensity of sensory stimulation provided to the subject based on a comparison of the previous spindle density to the recent spindle density and/or the previous spindle frequency to the recent spindle frequency, wherein controlling the means for providing sensory stimulation includes, responsive to the recent spindle density and the previous spindle density being determined, increasing the intensity of the sensory stimulation responsive to an increase in the recent spindle density relative to the previous spindle density;
means for detecting a possible arousal event based on the output signals;
means for, responsive to detecting the possible arousal event, causing the means for providing sensory stimulation to cease providing sensory stimulation;
means for determining whether the possible arousal event was a false arousal event; and
means for, responsive to determining that the possible arousal event was a false arousal event, causing the means for providing sensory stimulation to resume providing sensory stimulation with an intensity determined based on the recent spindle density relative to the previous spindle density and/or the recent spindle frequency relative to the previous spindle frequency.

12. The system of claim 11, wherein the means for providing sensory stimulation are configured such that the sensory stimulation comprises audible tones, and wherein the means for controlling the means for providing sensory stimulation are configured to cause the means for providing sensory stimulation to increase a volume of the audible tones responsive to the increase in the recent spindle density relative to the previous spindle density or, responsive to the recent spindle frequency and the previous spindle frequency being determined, a decrease in the recent spindle frequency relative to the previous spindle frequency.

13. The system of claim 11, wherein the means for providing sensory stimulation are configured such that the sensory stimulation comprises audible tones, and wherein the means for controlling the means for providing sensory stimulation are configured to cause the means for providing sensory stimulation to decrease a volume of the audible tones responsive to a decrease in the recent spindle density relative to the previous spindle density or, responsive to the recent spindle frequency and the previous spindle frequency being determined, an increase in the recent spindle frequency relative to the previous spindle frequency.

14. The system of claim 11, wherein the means for generating output signals are configured such that the output signals convey information related to a sleep stage of the subject during the sleep session; and wherein the system further comprises means for determining the sleep stage of the subject based on the output signals and controlling the means for providing sensory stimulation to adjust the intensity of the stimulation based on the determined sleep stage.

\* \* \* \* \*